(12) United States Patent     (10) Patent No.: US 9,278,208 B1
Gilson et al.     (45) Date of Patent: Mar. 8, 2016

(54) SPATIAL-TEMPORAL DEEP BRAIN STIMULATION METHODS AND SYSTEMS

(75) Inventors: Richard D. Gilson, Oviedo, FL (US); Nizam Razack, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 687 days.

(21) Appl. No.: 13/250,362

(22) Filed: Sep. 30, 2011

Related U.S. Application Data

(60) Continuation-in-part of application No. 11/837,138, filed on Oct. 5, 2007, now Pat. No. 8,032,231, which is a division of application No. 10/969,420, filed on Oct. 20, 2004, now Pat. No. 8,024,049.

(60) Provisional application No. 60/586,468, filed on Jul. 8, 2004, provisional application No. 60/512,660, filed on Oct. 20, 2003.

(51) Int. Cl.
    *A61N 1/36*     (2006.01)
    *A61N 1/05*     (2006.01)

(52) U.S. Cl.
    CPC ............ *A61N 1/0534* (2013.01); *A61N 1/0539* (2013.01); *A61N 1/36067* (2013.01); *A61N 1/36064* (2013.01); *A61N 1/36082* (2013.01)

(58) Field of Classification Search
    CPC ........... A61N 1/36067; A61N 1/37282; A61N 1/0534
    USPC .................................................. 607/45, 116
    See application file for complete search history.

(56) References Cited

U.S. PATENT DOCUMENTS

| | | | |
|---|---|---|---|
| 3,628,538 | A | 12/1971 | Vincent |
| 5,474,574 | A | 12/1995 | Payne |
| 5,479,934 | A | 1/1996 | Imran |
| 5,707,396 | A | 1/1998 | Benabid |
| 5,716,377 | A | 2/1998 | Rise |
| 5,833,709 | A | 11/1998 | Rise |
| 6,038,480 | A | 3/2000 | Hrdlicka |
| 6,301,492 | B1 | 10/2001 | Zonenshayn |
| 6,366,813 | B1 | 4/2002 | DiLorenzo |
| 6,539,263 | B1 | 3/2003 | Schiff |
| 6,597,954 | B1 | 7/2003 | Pless |
| 6,618,623 | B1 | 9/2003 | Pless |
| 8,024,049 | B1 * | 9/2011 | Gilson et al. ................... 607/139 |
| 8,032,231 | B1 * | 10/2011 | Gilson et al. ................... 607/139 |
| 2002/0072785 | A1 * | 6/2002 | Nelson et al. .................... 607/60 |
| 2002/0099412 | A1 * | 7/2002 | Fischell et al. .................... 607/3 |

(Continued)

*Primary Examiner* — Carl H Layno
*Assistant Examiner* — Jennifer Ghand
(74) *Attorney, Agent, or Firm* — Timothy H. Van Dyke; Beusse, Wolter, Sanks & Maire, PLLC

(57) ABSTRACT

Methods, systems, and devices for a deep brain stimulation device using miniaturized components that allow integration with the implanted probe, and includes a skull-sited housing having all the controls and battery power supply for sensing events and generating and transmitting pulses in response to the sensed event. A processor based controller with memory within the skull-sited housing for executing monitoring instructions for sensing initiation of an unwanted electro-physiologically signaled event and recording the event in memory and triggering instructions for activating the stimulator to generate and record a treatment pulse in response to the sensed event and an interface between the processor based controller and a treatment provider for downloading the recorded event and treatment response and modifying the monitoring and triggering sets of instructions.

9 Claims, 13 Drawing Sheets

(56) References Cited

U.S. PATENT DOCUMENTS

| | | |
|---|---|---|
| 2002/0183817 A1 | 12/2002 | Van Venrooij |
| 2002/0188330 A1 | 12/2002 | Gielen |
| 2003/0023297 A1 | 1/2003 | Byers |
| 2003/0085684 A1 | 5/2003 | Tsukamoto |
| 2003/0120324 A1* | 6/2003 | Osborn et al. ............ 607/60 |
| 2003/0130706 A1 | 7/2003 | Sheffield |
| 2003/0149457 A1 | 8/2003 | Tcheng |
| 2003/0181954 A1 | 9/2003 | Rezai |
| 2004/0172090 A1 | 9/2004 | Janzig |
| 2005/0143790 A1 | 6/2005 | Kipke |
| 2005/0159799 A1 | 7/2005 | Daglow |
| 2005/0171587 A1 | 8/2005 | Daglow |
| 2007/0225773 A1* | 9/2007 | Shen et al. ............ 607/45 |

* cited by examiner

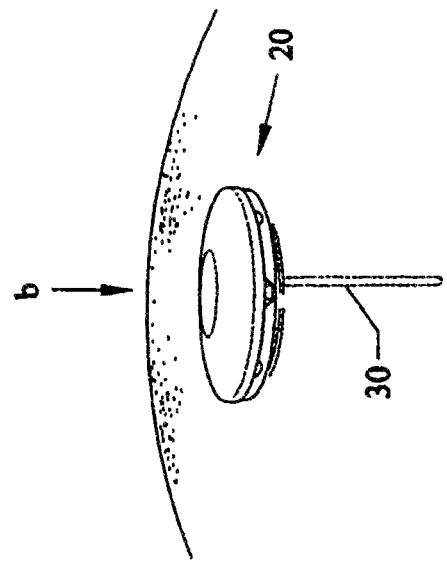
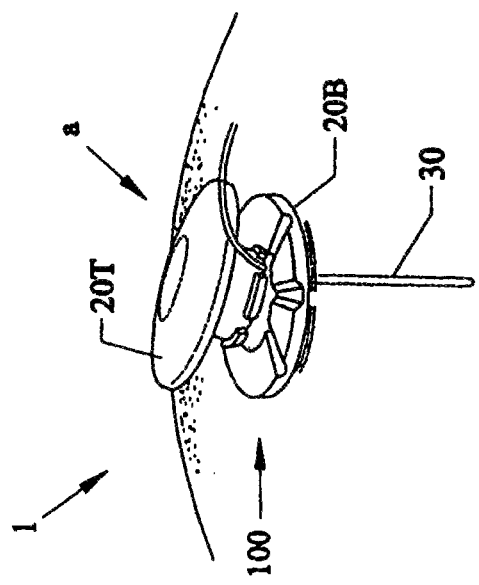

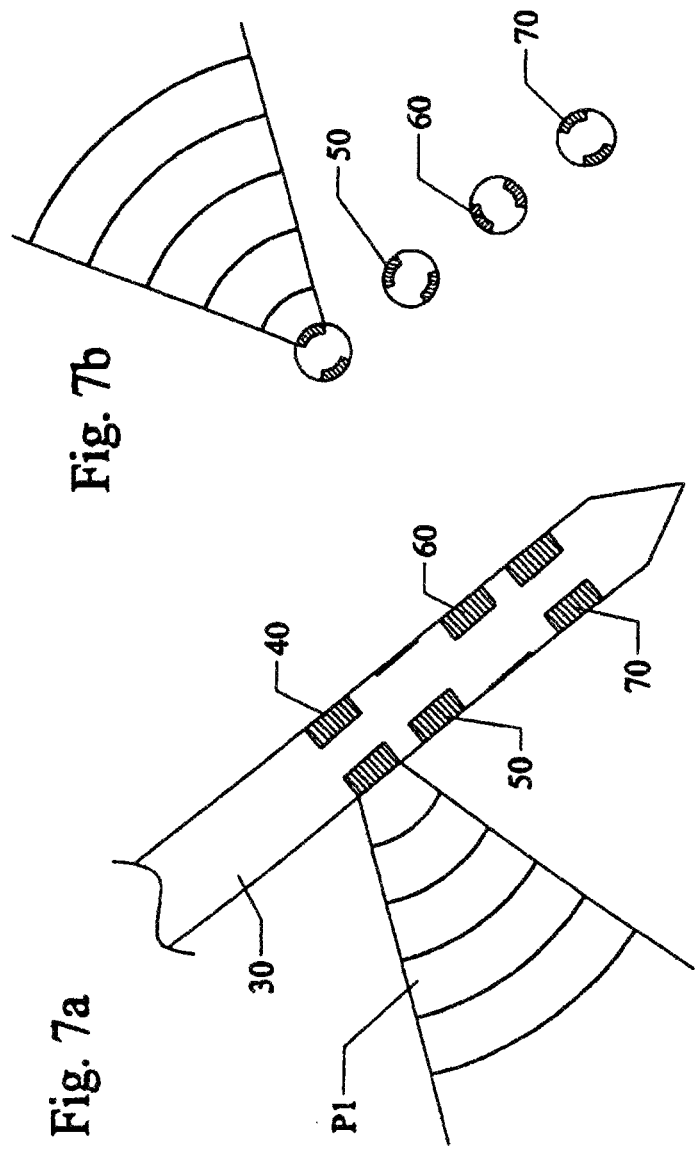

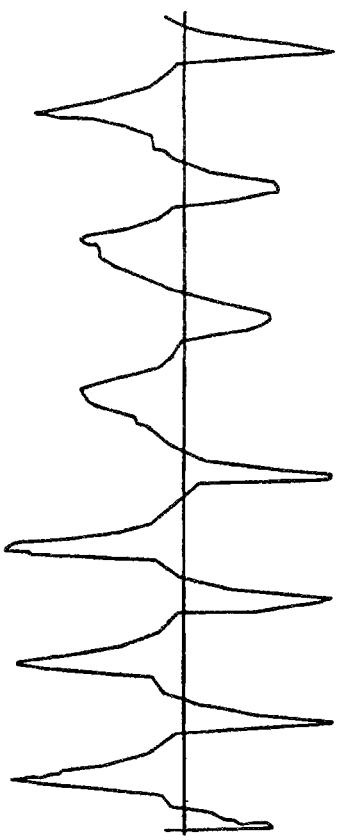

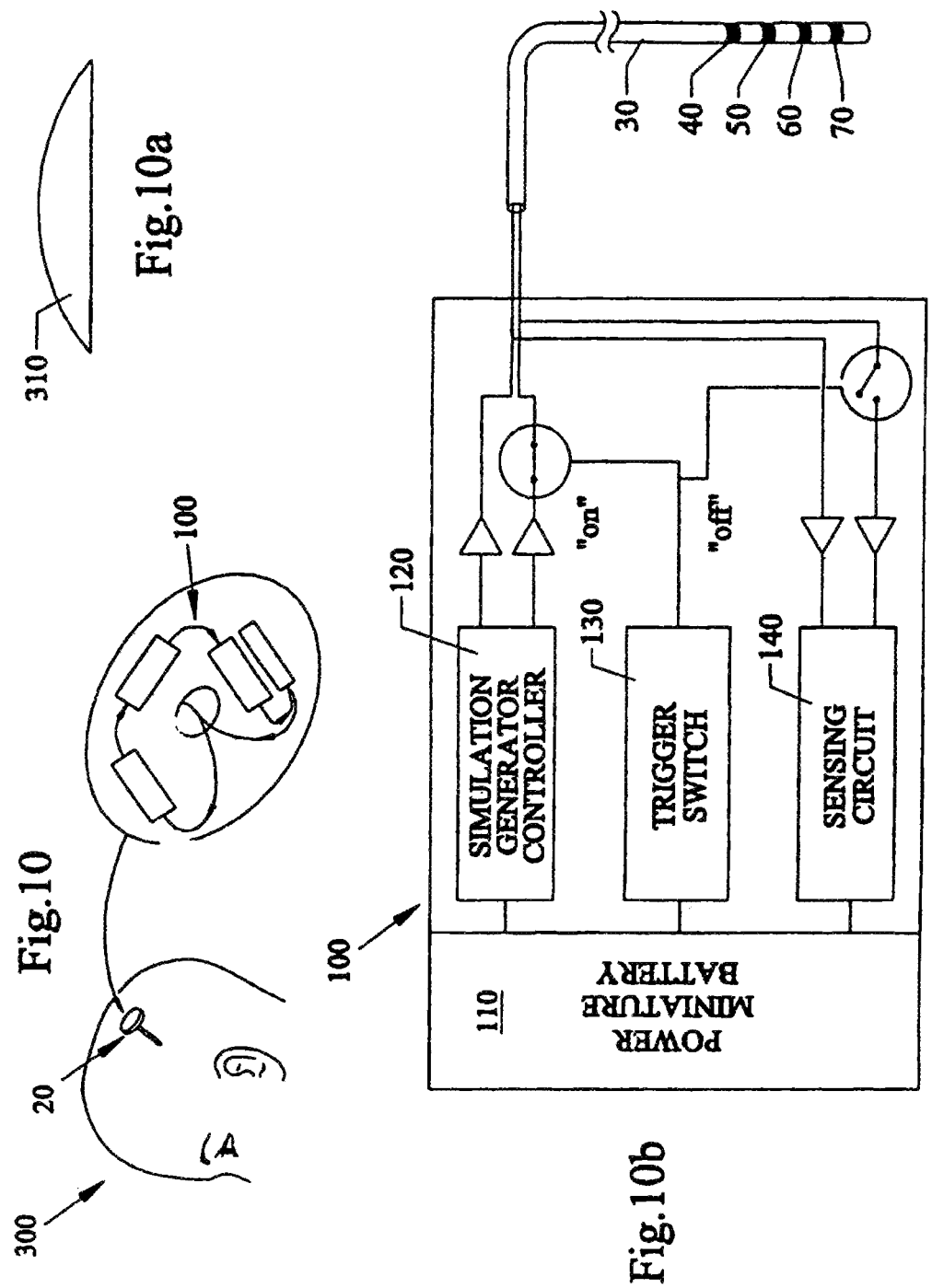

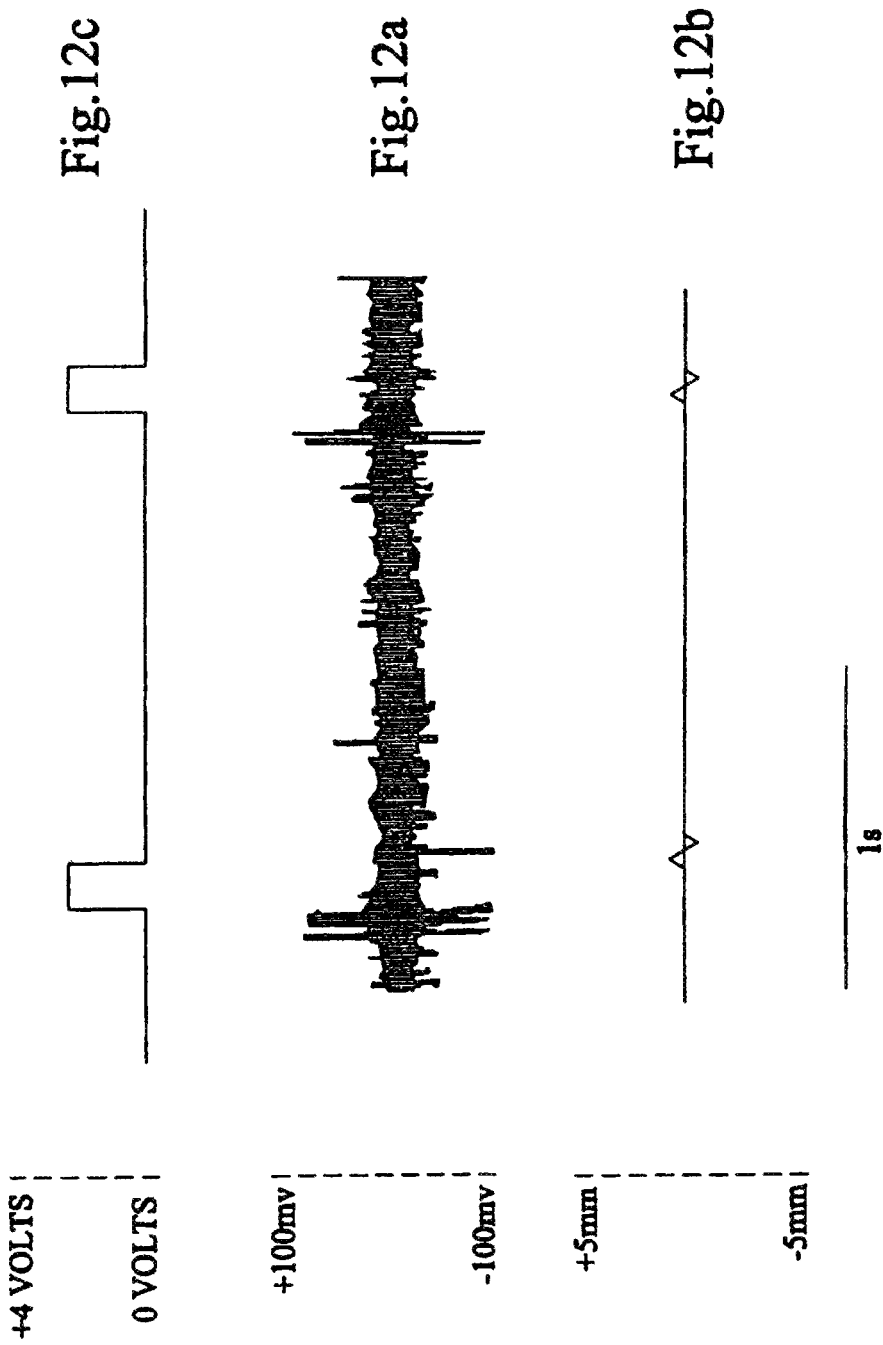

SPATIAL-TEMPORAL DEEP BRAIN STIMULATION METHODS AND SYSTEMS

This application is a continuation-in-part of U.S. Pat. No. 8,032,231, issued on Oct. 4, 2011, which is a divisional of U.S. Pat. No. 8,024,049 filed issued on Sep. 20, 2011, which claims the benefit of priority to U.S. Provisional Patent Application Ser. Nos. 60/512,660 filed Oct. 20, 2003, and 60/586,468 filed Jul. 8, 2004.

FIELD OF INVENTION

This invention relates to deep brain stimulation (DBS), in particular to methods, systems, and devices for enhancing both efficacy and efficiency of "in-vitro" electrical stimulation known to inhibit symptoms of neurological diseases, disorders, and the like, and utilizes: (a) methods that tailor the direction and shape of electrical fields towards the area of best effect; (b) systems that interactively trigger stimulation to terminate the onset of tremors, and such; (c) devices that use the aforementioned efficiencies to reduce power and allow for self-contained miniaturization at the implant site, thereby improving patient comfort; (d) an implanted integrated circuit and memory integrated with the device for recording physiological effects of the implanted device and (e) an interface for remote programming and downloading recorded physiological data.

BACKGROUND AND PRIOR ART

A first line of defense considered for most neurological disorders is treatment with psychoactive medicines, prior to any surgical intervention. Psychoactive medicines or drugs are those capable of acting on the nervous system and affecting mental states and behavior. Many physiological mechanisms are aided by such drugs, but these medicines have unwanted side effects, drug interactions, and long-term physiological tolerances that render the drug less effective over time.

In the case of Parkinson's disease that serves as the exemplar disorder herein, the underlying etiology is that neurons, located in the substantia nigra of the mid-brain, for some unknown reason begin to produce less dopamine. As these neurons progressively and relentlessly deteriorate over years, less dopamine dramatically affects the motor control of the basal ganglia and thus outward behavior and everyday living. An estimated 1.5 million Parkinson's patients have a visible cluster of diagnostically significant and debilitating Parkinson's symptoms, typically tremors, stiffness, slowness, and balance. Patients describe the internal feeling as frozen still in the "set" stage of the "ready, set, go" sequence that started of a race.

The "gold" standard treatment for Parkinson's is frequent daily administration of an indirect dopamine replacement, L-Dopa, a psychoactive drug that crosses the blood-brain barrier, and then alters form to produce dopamine as a supplement to the brain's own production. This therapy, while initially quite beneficial, typically can lose much of its effectiveness over about five years, wherein patients have to take progressively larger and more frequent doses until eventually the result becomes inadequate. Without alternative drug therapies, patients are left to suffer both the ravages of primary symptoms and the manifestations resulting from the prolonged use of the drug itself, principally the repetitive spasmodic motions of dyskinesia. More than one million people endure these symptoms, including such notables as the Pope, Muhammad Ali, and Billy Graham, while thousands of others including Michael J. Fox have turned to surgical approaches.

Past surgical techniques treated symptoms of these diseases by selectively and permanently destroying or ablating structural areas in the brain. The net effect is to "shut the door", in a neurological fashion, before dysfunctional brain signals are sent to the muscles, thereby relieving many symptoms. The advantage of surgical ablation is that it reduces the reliance on drug therapy with its attendant side effects. The disadvantage is that the procedure is irreversible. This may render such patients as unacceptable candidates for newly discovered techniques/therapies, such as stem cell implantation or viral transport of genome-altered DNA (deoxyribonucleic acid), both of which show promise in helping to augment or even to regenerate the natural production of dopamine as well as a number of other substances involved in neurological disorders.

Certain neurological disorders that produce debilitating motor symptoms are now being treated with Deep Brain Stimulation (DBS) through-skull implanted electrodes see FIG. 1 below. DBS essentially reversibly alters the local neurological structure(s) around the tip of an electrode implanted on the brain with electrical pulses that reduce or stop disabling symptoms, such as, but not limited to, severe tremor and rigidity found in Parkinson's disease.

DBS functionally has the advantage of emulating ablation by changing the firing characteristics of nearby neurons, but it does so only while the pulsed stimulation persists. Since the structures remain intact and undamaged, when DBS is turned "off" these structures reactivate and symptoms return, unless otherwise treated. Thus, DBS overcomes the chief disadvantage of ablation in that it allows implanted simulators to be withdrawn later for new techniques, with minimal residual effects. In 1998, the Federal Drug Administration (FDA) approved DBS as an alternative for, or as an adjunct to powerful psychoactive drugs (neuro-medicines) burdened with strong and often unacceptable side effects.

The only FDA approved DBS apparatus is currently being sold by Medtronic, Inc., 710 Medtronic Parkway, Minneapolis, Minn. 55432-560, see FIGS. 2 and 3 below, although other companies have substantial interests in implantable neurostimulation devices for a variety of neurological disorders, such as Advanced Bionics, Corp., 12740 San Fernando Road, Sylmar, Calif. 91342; see "http://www.advanced bionics.com." However, there are problems with the approved apparatus.

At the very least, the presently approved apparatus is cumbersome and uncomfortable for many in its present form. As an outgrowth of legacy components from heart "pacemakers," it consists of one or two remote stimulator/battery packs embedded under muscle tissue in the upper chest area, and requires subcutaneous leads up along the neck to the skull entry point. All these components are subject to corrosion and breakage, as well as to resistance or attacks by the body itself attempting by encapsulate it or dissolve it, leading to infection.

Medtronic currently uses a product called a Soletra™ Neurostimulator (see FIG. 4 below) to generate a continuous series of electrical pulses, typically at about 2-4 volts, to electrode(s) implanted in specific brain areas. Neurons, normally operating in the tens of milli-volts range, are massively over-stimulated by such voltage and temporally altered, thereby inhibiting the expression of certain motor dysfunctions. Pulse voltage is usually adjusted somewhat depending on the proximity of the electrode(s) to the targeted area, e.g., more voltage is needed for target variations. Typical pulse rates range around 130-185 pulses/second.

This combination of large amounts of voltage, amperage, and duty cycle creates a power drain that normally requires a non-renewable battery replacement in about 3-5 years, at a price of about $10,000. Many patients turn "off" the stimulation when going to sleep while tremor is quelled, in order to conserve power. Current DBS stimulator(s) are designed to be turned "off" or "on" using a magnetic-switch placed briefly near the associated electronics.

Thus, without considering the remote apparatus itself, or the power requirements of the present design, a goal in this field should be to reduce stimulation-related side effects and complications caused by stimulating in the vicinity of the target. Two key objectives to meeting that goal are for the surgical implant to hit the center of a targeted cellular region, often not more than 2 mm across in any direction, and for the current field to stimulate the appropriate cells for symptom reduction or cessation, without triggering side effects in adjacent structures.

While the surgical techniques themselves are well documented, the surgery is still a unique combination of art and science [see Lozano, Andres M. (Ed): Movement Disorder Surgery: Progress in Neurological Surgery, vol. 15, pp. 202-208, Basel, Switzerland: Karger A G, 2000, ISBN 3-8055-6990-4.].

A key to a successful outcome is the precise positioning and placement of the electrode(s), aided pre-operatively by vast improvements in brain imaging techniques, but nevertheless requiring considerable surgical skill and judgment. Beside normal variations in brain structures themselves adding to the difficulty of targeting, during surgery the brain moves with each heartbeat, while its size and position vary somewhat as a result of the surgical probe itself altering internal pressure. During the procedure, the use of fluoroscope imaging assists y-z axis positioning, and awakening of the patient while in the operating room for testing of clinical signs can reveal and help avoid untoward side effects. However, but the final outcome can only be assessed post-operatively. Results can vary by patient and over time. Some post-surgical adjustment is normally done with electrical parameters and z-axis programming of one or more of the electrode contacts available on the current DBS electrode, as is described below, but not to the extent that many physicians would like and not with respect to the x-y axis.

Current DBS electrodes have four (4) circumferential contacts that radiate current in a 360 degree configuration. This means that with any degree off-target, or unnecessary stimulation even on target adjacent cells are exposed to current and potential side effects. While some of these side effects may be adjustable when electrical parameters are altered, or even reversible when the stimulation is shut down, but the cost is decreased efficacy of stimulation on the symptoms. For example, in sub-thalamic nucleus DBS, stimulation-induced side effects may include increased dyskinesias, blepharospasm or so called "eyelid-opening apraxia," confusion/memory disturbances, personality changes, mood changes, apathy, cognitive changes, dysphonia/dysarthria, and such.

Medtronic Inc. has proposed a "Directional Brain Stimulation and Recording Leads, title, in U.S. Published Patent Application 2002/0183817 to Van Venrooij et al., which is incorporated by reference. The proposed technique uses a "controller" as shown and referenced to FIG. 32 for recording "brain activity signals" to activate electrodes. However, this technique requires continuously generating pulsed type signals once the electrodes are activated whether or not a brain type tremor has ended, which would result in needless, unwanted and potentially excessive electrical current being continuously generated inside the brain. The more unnecessary pulse type signals, the more undesirable side effects to the patient, for example, in thalamic DBS, stimulation-induced side effects may include paresthesias, muscular cramps, dystonia, dizziness, dysarthria, gait and balance disturbances, limb ataxia, impaired proprioception, and decreased fine motor movements.

Additionally, this technique would require excessive power to operate, which is not only expensive since battery power supplies would need to be regularly replaced but also require large card-deck size batteries that must be mounted inside of the patient's upper chest area. This proposed Medtronic technique would also be prone to circuit problems since the electrodes would be simultaneously operating as both transmitters and sensors, causing excessive and unnecessary power drain, shortening the lifespan of any batteries being used as well as increasing the costs for replacing the batteries.

According to the Movement Disorder Society© 2002, "Deep brain stimulation for the alleviation of movement disorders and pain is now an established therapy. However, very little has been published on the topic of hardware failure in the treatment of such conditions irrespective of clinical outcome. Such device-related problems lead to significant patient morbidity and increased cost of therapy in the form of prolonged antibiotics, in-patient hospitalization, repeat surgery, and device replacement [Joint, C., Nandi, D., Parkin, S., Gregory, R., and Aziz, T. *Hardware-Related Problems of Deep Brain Stimulation*. Movement Disorders, Vol. 17, Suppl. 3, 2002, pp. S175-S180.]

Thus, the need exists for solutions to the problems encountered in the prior art.

SUMMARY OF THE INVENTION

A first objective of the present invention is to provide for deep brain stimulation (DBS) methods, systems and devices that avoid implanting large card-deck size batteries remotely in the chest area and the use of vulnerable wire leads under the skin from the chest area to connect with the implanted electrode on the skull.

A second objective of the present invention is to provide for deep brain stimulation (DBS) methods, systems and devices that allow for substantially all electronics including but not limited to an on-site battery pack to be located at or near the implanted electrodes on the skull.

A third objective of the present invention is to provide for deep brain stimulation (DBS) methods, systems, and devices that can use substantially less power than current DBS techniques and apparatus.

A fourth objective of the present invention is to provide for deep brain stimulation (DBS) methods, systems and devices, that do not generate a continuous series of un-synchronized pulses that are continuously generated whether they are needed or not.

A fifth objective of this invention is to provide for deep brain stimulation (DBS) methods, systems and devices, to generate pulses on demand. Specifically, inhibiting pulse(s) can be interactively triggered by the onset of each unwanted electro-physiologically signaled event, such as at the beginning of a tremor.

A sixth objective of the present invention is to provide for deep brain stimulation (DBS) methods, systems and devices that are more compact, easier to use and last longer than current DBS techniques, thereby improving patient comfort.

A seventh objective of the present invention is to provide for shaped electrodes and methods by using the electrode contacts in deep brain stimulation (DBS) methods, systems and devices, that orient configured electrical fields to specific points, preferentially directing current a targeted cellular region and facilitating the clinical effect. The best direction of the shaped current can be determined intra-operatively through recordings and clinical testing along the "X-Y" plane.

An eighth objective of the present invention is to use shaped electrodes in deep brain stimulation (DBS) methods, systems and devices, in order to decrease off-target current stimulation, thereby minimizing or eliminating exposure to adjacent cellular regions that produce side effects.

A ninth objective of the present invention is to use the decreased electrical "aperture" of shaped electrodes in deep brain stimulation (DBS) methods, systems and devices, in order to maintain current density on the target region, but with less overall current flow and less battery drain over time.

A tenth objective of the present invention is to include an integrated circuit and memory integrated with the device for recording physiological effects of the implanted device and an interface for remote programming and downloading recorded physiological data.

Methods, systems and devices are provided for deep brain stimulation (DBS) in response to a sensed brain tremor that includes a single cylindrical disc housing with a single bottom housing with side edges and a single removable top with perimeter side edges that overlap the side edges of the single bottom housing, a single elongated lead extending between a center portion of the bottom of the single cylindrical disc housing with a plurality of electrodes with each electrode being used to both sense a single brain tremor and generate pulses therefrom, the single lead being adapted to be implanted into only a single opening in the skull while the single cylindrical disc housing remains mounted as cap on top of the skull of the user, a pulse stimulator inside a compartment of the single cylindrical disc housing and only being activated to generate a pulse stimulation upon sensing a tremor from one of the plurality of electrodes, sensing detection circuitry, controls for activating the pulse stimulator upon sensing of the single brain tremor and deactivating the pulse stimulator when a tremor is not being sensed, and a battery power supply for providing power to the pulse stimulation only upon sensing the single brain tremor and along with the controls turning off the pulse stimulator after the sensing detection circuitry has been turned on.

The plurality of electrodes can include four electrodes for transmitting and receiving on the single elongated lead; or one of the electrodes senses the tremor, and at least the same electrode generates the pulses therefrom targeting a location which emits the single brain tremor; or at least two of the electrodes senses the tremor, and at least one of the two electrodes generates the pulses therefrom targeting a location which emits the single brain tremor.

The deep brain stimulation device can also include a processing device with memory to execute a set of instructions to record physiological data of the sensed tremor and a response to the sensed tremor and can also include an interface for downloading the recorded physiological data. The interface can be a wireless interface to automatically transmit recorded physiological data to an external computer the interface can be a wireless interface to allow a treatment provider to modify the automatic response to the sensed tremor.

A remote physician can receive video feedback using a video camera to provide the visual feedback of the patient receiving deep brain stimulation via an internet connection to a remote location physician and the interne connection can be an online video telephone service transmitting realtime audio and video.

Another embodiment provides a method for deep brain stimulation in response to a sensed brain tremor that includes providing a single cylindrical disc housing with a single bottom housing with side edges and a single removable top with perimeter side edges that overlap the side edges of the single bottom housing, a single elongated lead extending between a center portion of the bottom of the single cylindrical disc housing with a plurality of electrodes with each electrode being used to both sense a single brain tremor and generate pulses therefrom, the single lead being adapted to be implanted into only a single opening in the skull while the single cylindrical disc housing remains mounted as cap on top of the skull of the user. One or more of the plurality of electrodes senses a single brain tremor and generates a pulse stimulation from a pulse stimulator upon sensing the tremor from one of the plurality of electrodes. The deep brain stimulation device controls activation of the pulse stimulator upon sensing of the brain tremor and deactivation the pulse stimulator when a tremor is not being sensed, and includes a battery power to the pulse stimulation only upon sensing the single brain tremor and along with the controls turning off the pulse stimulator after the sensing detection circuitry has been turned on.

The deep brain stimulation method can include recording physiological data of the sensed tremor and responses to the sensed tremor and transmitting the recorded physiological data to a remote monitoring location. Additionally, visual images of the patient receiving treatment can be transmitted to a remote monitoring location and the remote physician can instruct a treatment provider to modify the pulse stimulator based on the recorded physiological data and the visual images of the patient.

Another embodiment provides a deep brain stimulation system with remote monitoring controls that includes a cap mounted housing having an elongated lead extending from the cap mounted device, the lead adapted to be implanted into a head of a patient, a plurality of electrodes on the lead for sensing tremors and generating pulses therefrom directed toward the tremors, a processor based controller having monitoring instructions for sensing initiation of an unwanted electro-physiologically signaled event and recording the event in memory, and a set of triggering instructions for activating a stimulator to generate at least one treatment pulse from the electrodes and record physiological data from the treatment pulse in the memory, a transmission medium for sending the recorded physiological data to a remote monitoring location, and another transmission medium for sending treatment instructions to a treatment provider station for modifying the monitoring and triggering sets of instructions in the processor. The system can include a video camera for providing feedback images via an internet connection to the remote monitoring location, wherein the treatment instructions are based on both the recorded physiological data and the visual feedback images.

Similarly, a method is provided for a remotely monitoring a deep brain stimulation system that includes providing a cap housing with a lead line having a plurality of electrodes that is adapted to be implanted into a head of a patient, sensing at least one brain tremor at one or more of the plurality of electrodes, generating a pulse stimulation from a pulse stimulator upon sensing the tremor from one of the plurality of electrodes, recording physiological data of the sensed tremor and responses to the sensed tremor, and transmitting the recorded physiological data to a remote monitoring location, and modifying at least one operating parameter of the pulse stimulator based on feedback from the remote monitoring location. The method can include recording visual images of a patient being treated by the pulse stimulator, transmitting the visual images of the patient receiving treatment to the remote monitoring location, and modifying at least one operating parameter of the pulse stimulator based on feedback from the remote monitoring location having received both the recorded physiological data and the transmitted visual images of the patient. The method can also include instructing a treatment provider to modify the pulse stimulator based on the recorded physiological data and the visual images of the patient.

Further objects and advantages of this invention will be apparent from the following detailed description of the presently preferred embodiments, which are illustrated schematically in the accompanying drawings.

BRIEF DESCRIPTION OF THE FIGURES

FIG. 5a shows an open view of a miniaturized integrated battery/stimulator apparatus of the subject invention.

FIG. 5b shows a closed view of the apparatus of FIG. 5a.

FIG. 7a shows enlarged side views of four shaped electrodes with projected fields used in the apparatus of FIGS. 5a, 5b and 6.

FIG. 7b illustrates the axial views of the four shaped electrodes of FIG. 7a with respective projected fields.

FIG. 8a shows a recording trace graph of neuronal impulse bursts in mill volts verses time that can occur with an untreated patient.

FIG. 8b shows a trace graph of associated tremor displacement for FIG. 8a in millimeters verses time that can occur with the untreated patient.

FIGS. 10, 10a and 10b shows a layout of the electronic components that can be used in the apparatus of FIGS. 5a, 5b, 6 along with the triggering algorithm of FIG. 9.

FIG. 12a shows a trace graph of the neuronal impulse bursts in milli-volts verses time of a patient being treated from being treated by the subject invention.

FIG. 12b shows a trace graph of the associated tremor displacement for FIG. 12a verses time of the patient being treated by the subject invention.

FIG. 12c shows the single pulses that occur with the subject invention technique which results in the trace graphs of FIGS. 12a-12b.

DESCRIPTION OF THE PREFERRED EMBODIMENTS

Figure 1:
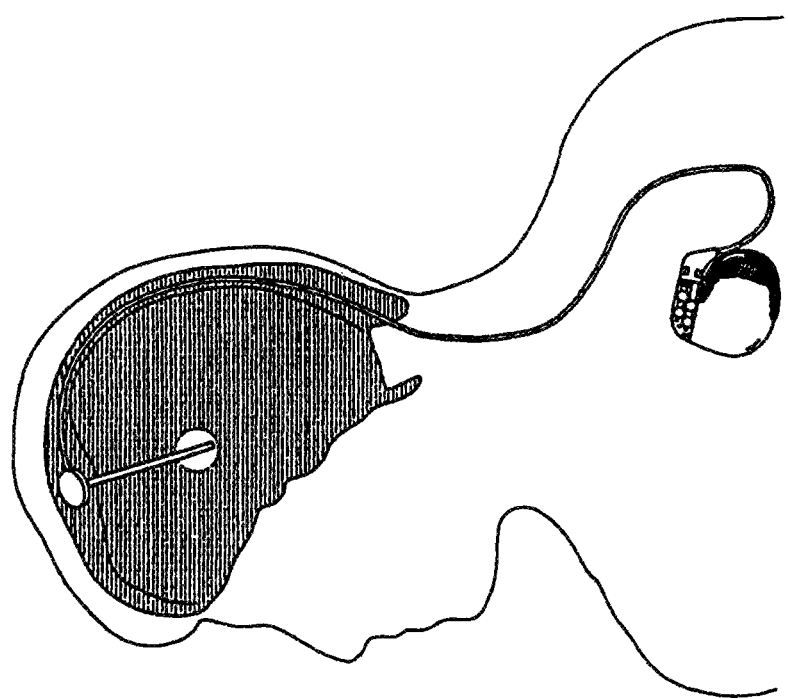
FIG. 1 shows a deep brain stimulation (DBS) apparatus of the prior art.
Figure 2:
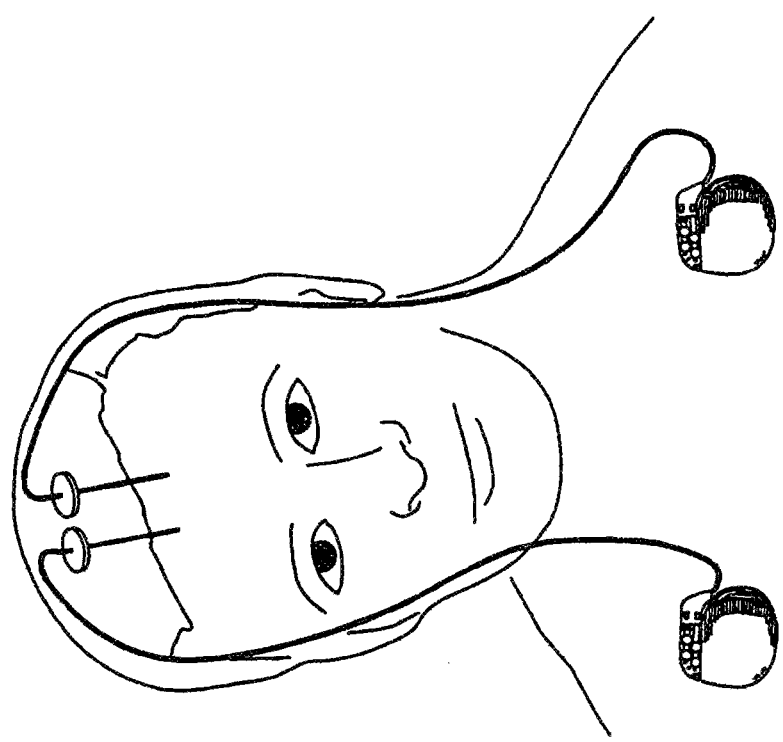
FIG. 2 is a front view of the current prior art DBS of FIG. 1.
Figure 3:
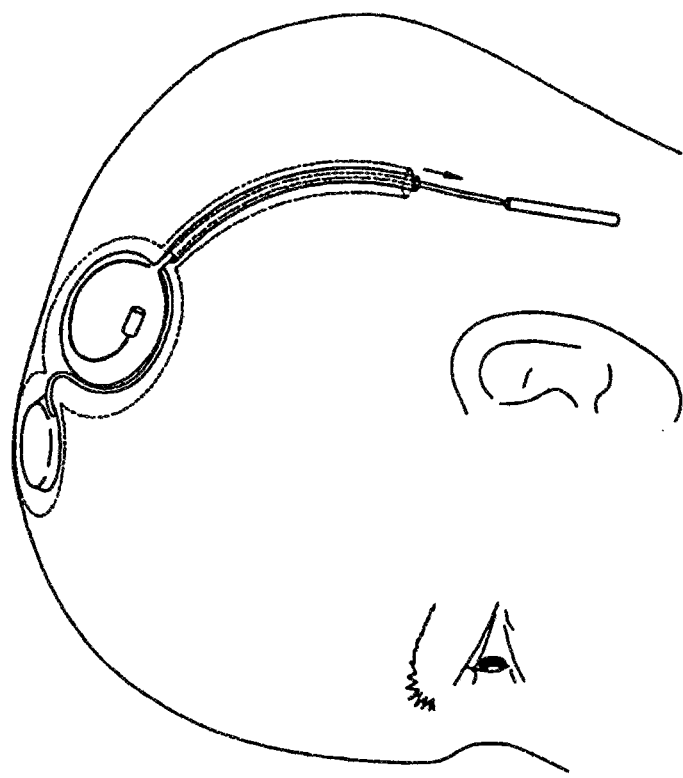
FIG. 3 shows DBS head-mounting details of the prior art of FIGS. 1-2.
Figure 4:
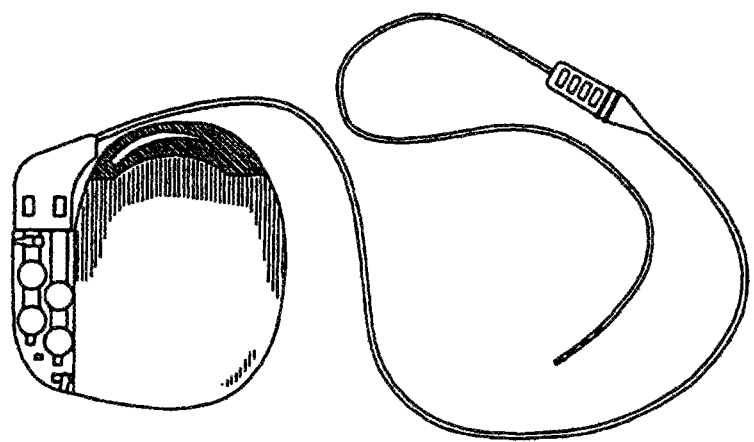
FIG. 4 shows another prior art product device.

Before explaining the disclosed embodiments of the present invention in detail it is to be understood that the invention is not limited in its applications to the details of the particular arrangements shown since the invention is capable of other embodiments. Also, the terminology used herein is for the purpose of description and not of limitation.

This invention provides methods, systems and devices to reduce power demands substantially for DBS (deep brain stimulation), allowing for miniaturized type components to be integrated with the implanted probe(s) themselves, see FIGS. 5a, 5b, 6 and 10. A preferred embodiment provides methods and apparatus for a remote physician to receive both physiological feedback and visual feedback from the patient on results of the treatment and allows the remote physician to modify the treatment based on the feedback.

The invention avoids implanting large and cumbersome card-deck size batteries in the chest area and the use of vulnerable wire leads under the skin from the chest area to connect with the implanted electrode(s) on the skull. Notably, the remote stimulator/battery with its associated wiring are the chief source of complaints in the use of this technique. Other advantages of this invention are also apparent.

The invention substantially differs from that used in current techniques. Rather than generating a continuous series of un-synchronized pulses that act whether needed or not, pulses can be generated on demand. Specifically, inhibiting pulse(s) can be interactively triggered by the onset of an unwanted electro-physiologically signaled event, such as the beginning of a tremor. The same electrode(s) that now serves as a one-way input also can serve as a bi-directional conduit to sense the electrical beginnings of the event itself as well as delivering the pulse(s). Thus, with appropriately tailored, triggering algorithms, a preferred example of which is described below in reference to FIG. 9, an inhibiting pulse can be timed for delivery so as to suppress the event's full expression.

Using this approach, power drain reductions of conservatively 85% or more are achievable, with the percentage depending on the neurological events of interest. For example, most tremors are less than approximately 10 tremor cycles per second, and can be far less when the tremor is interrupted by another intentional activity such as purposeful movement, as in the case of Parkinson's disease. Thus, the constant power drain can be reduced from approximately 150 stimulating pulses/second using the current techniques described in the prior art to now to as little as one stimulating pulse counteracting each tremor onset using interactive triggering.

Even greater power reductions are possible for "lower frequency" tremor, such as Essential tremor at approximately 5 to approximately 7 tremor cycles/second, or "low-frequency" Parkinson tremor at approximately 3 to approximately 5 tremor cycles/second.

With dramatically reduced power demands for DBS, this invention then allows for miniaturized components to be integrated with the skull cap attachment to the implanted probe(s) themselves, as shown in FIGS. 5a, 5b, 6 and 10. In the preferred embodiment, the deep brain stimulation device is configured in a vertical arrangement of four directional electrodes wherein one or more of the electrodes can sense the tremor and send a treatment pulse toward the area of the brain to treat the tremor.

Figure 6:
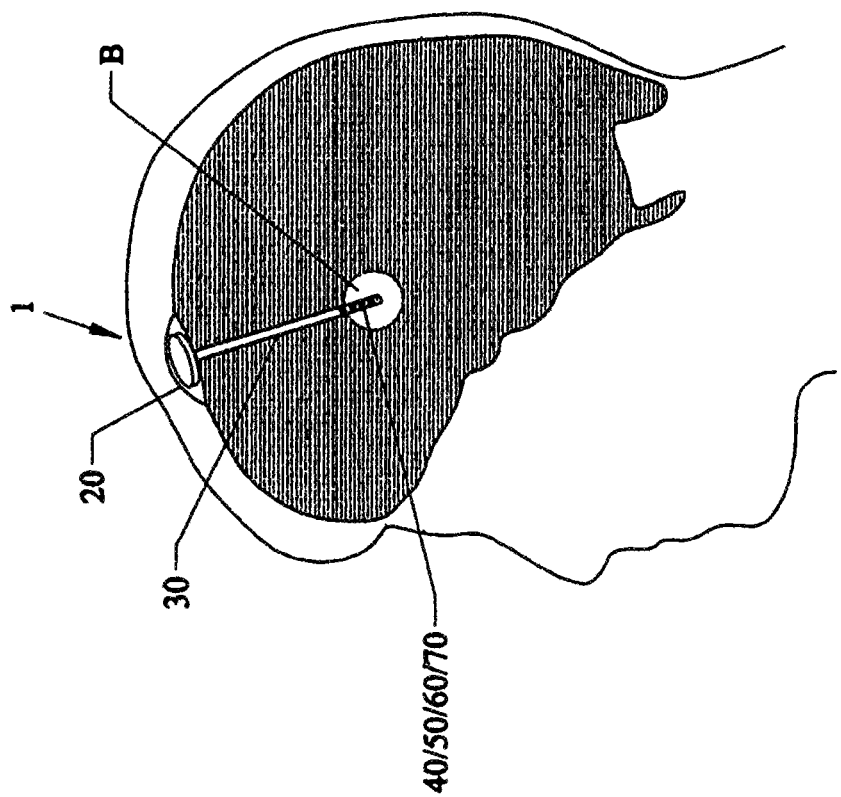
FIG. 6 shows the novel invention apparatus of FIGS. 5a-5b utilized in a head mounted application.

FIG. 5a shows an open view of a miniaturized integrated battery/stimulator apparatus 1 of the subject invention. FIG. 5b shows a closed view of the apparatus 1 of FIG. 5a. FIG. 6 shows the novel invention apparatus 1 of FIGS. 5a-5b utilized in a head mounted application.

Referring to FIGS. 5a-5b and 6, the hole cap 20 can include a top cover 20T, and bottom cylindrical disc housing 20B to house components 100 (which are described and shown in greater detail in reference to FIG. 10). Underneath the cap 20 can be a lead line 30, and approximately four (4) directional electrodes 40, 50, 60 and 70 attached thereon. FIG. 7a shows enlarged side views of four shaped electrodes with projected fields used in the apparatus of FIGS. 5a, 5b and 6. FIG. 7b illustrates the axial views of the four shaped electrodes of FIG. 7a with respective projected fields (i.e., P1 of FIG. 7a).

Referring to FIGS. 6, 7a and 7b, the electrodes 40-70 on the lead 30 can include a non-conducting material, such as but not limited to insulating material, and the like, on one side or on a portion of the electrode. Examples, of non-conducting material can include but are not limited to rubbers, elastomers, plastics, coated metals, and the like, and combinations thereof, and the like.

This nonconductive material can also be used to help direct electrical field emissions to one side or to more specific regions, and/or points, rather than to a 360-degree emission. The invention can include a lead 30 can having a single electrode with a nonconductive surface region.

Alternatively, more than one electrode can be used on the lead in series to one another. The nonconductive surface region can be applied on the same side of the electrodes, or to different side surface portions of the electrodes as needed. Additionally, different combinations can be used. For example, an upper electrode can emit up to 360 degrees while other electrodes are directed to emit in specific regions and/or points.

Additionally, circuitry can be added to control which electrodes are being emitted at selected time periods, and the like. For example, electrodes can be further programmed with a microprocessor, to activate simultaneously and/or sequentially, and/or staggered and/or over different combinations, and the like. The invention can use directional type electrodes, such as those shown and described in reference to U.S. Published Patent Application 2002/0183817 to Van Venrooij et al., which is incorporated by reference.

The miniaturized implantable electrode apparatus and stimulation systems can also include those described in United States Patent Application 20030023297, to Byers et al. filed on Jan. 30, 2003, which is incorporated by reference. This reference describes an eyelid stimulation system and circuitry that causes a paralyzed eyelid to close or open by passing an electrical stimulating current to a nerve.

The invention can be used to treat brain impulse bursts and the resultant physical extremity tremors that result therefrom. FIGS. 8a and 8b represent untreated brain impulse bursts and resultant physical extremity tremor outcome that are untreated. FIG. 8a shows the recording of impulse bursts from the brain B, that results from the leads 30 that are connected to the electrodes 40-70 (of the apparatus of FIG. 6). The large amplitude bursts represent the impulses that result in the tremors (impulses from brain to effected extremity). FIG. 8b represents an extremity that is being affected by the impulse (here for example, a single index right hand finger). A laser measuring sensor was aimed at the index finger to record the results shown in FIG. 8b. For example, a plus 5 mm apex reading would represent the finger moving forward from a horizontal plane, and −5 mm represents the finger moving aft in the horizontal direction.

Figure 9:
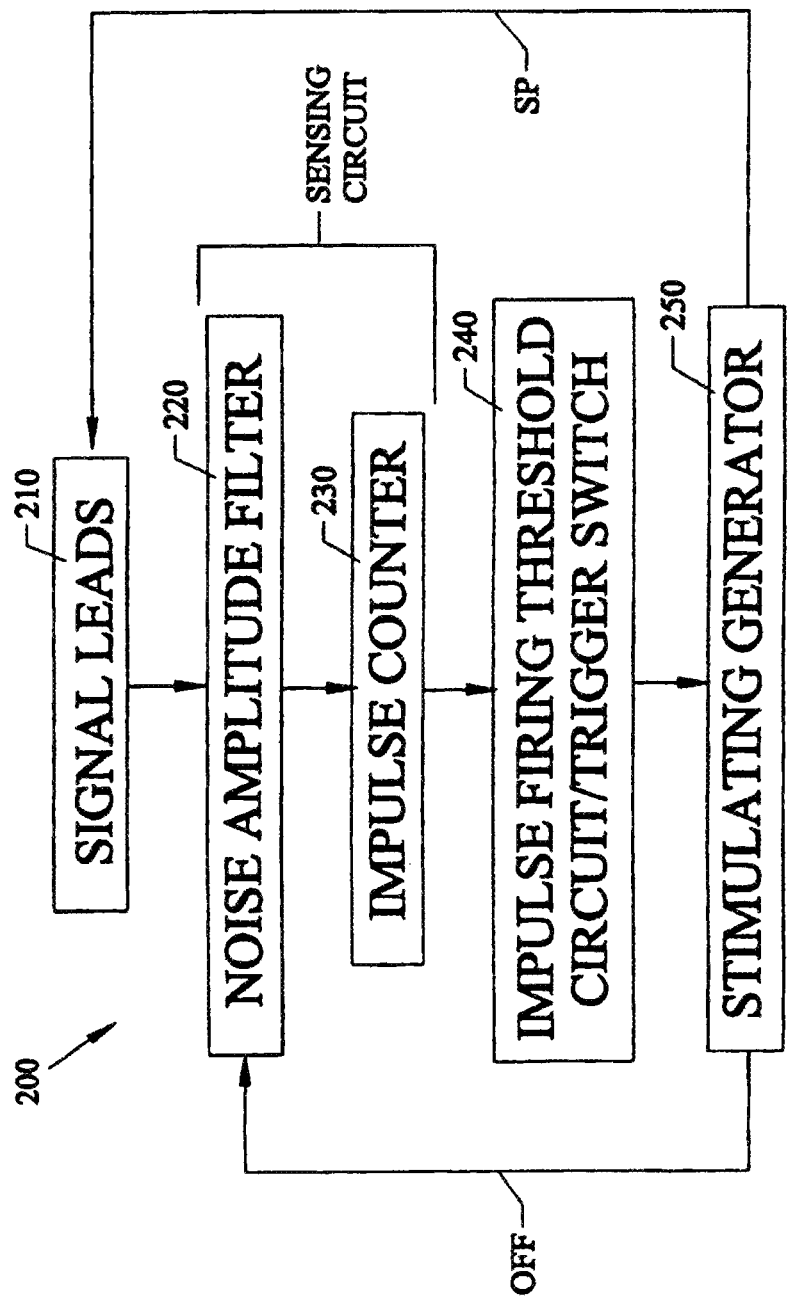
FIG. 9 shows an exemplary flow chart of a triggering algorithm steps that can be used with the invention.

The invention can use a triggering algorithm to selectively activate electrodes and treat effected parts of the brain where impulse bursts occur. FIG. 9 shows an example flow chart of a triggering algorithm steps that can be used with the invention. The triggering algorithm can take a number of forms or be adaptive, based on patient neuro-generative responses. In a simple illustrative form, not intended to be limiting, triggering sensing can be based on exceeding a threshold-firing rate measured in impulses/second.

FIG. 9 shows an exemplary triggering algorithm 200 for using the electrodes 40-70 of the preferred embodiment shown in the preceding figures that switches back and forth between a sensing mode and transmitting mode. In the first step 210, signals coming from leads 30 from the microelectrodes 40-70 in the implant receive a signal from the electrodes 40-70 (the first left trace signal from FIG. 8a) can be passed through a noise amplitude filter 220 (for example an high pass amplitude filter cutting off a low frequency of for example everything below approximately 20 mill volts is filtered out). Next during step 230, the filtered signal goes to an impulse counter, such as a clock counter which can count the number of impulses passing through, which can be represented in impulses per second. Next step 240, has an impulse firing threshold type circuit that can be used that filters out false alarms and allows for a selected threshold, such as for example, 5 impulses within 50 milli-seconds, would trigger the generator in step 250 to send a generated pulse SP back down the signal leads 30 to the electrodes 40-70.

When the generator is triggered, a signal can also be sent (along line Off) to simultaneously shut off the sensing mode of the electrodes, allowing the electrodes to be in a transmitting mode state. Sensing mode parameters of the electrodes 40-70 can be in approximately 20 to approximately 60 millivolts, while the transmitting/triggering range of the electrodes 40-70 can be approximately 2 to approximately 4 volts. The novel triggering algorithm 200 allows the electrodes 40-70 to be switched back and forth between transmitting and sensing modes without overloading the circuit components, and thus maximizing power usage during operation.

Once triggered, stimulation blocking continues until firing impulse firing rate drops below the critical threshold value. The sensing and stimulation can use the same micro-electrode leads, alternatively, wherein the sensing circuitry first uses an impulse counter/clock, then if threshold is exceeded, circuit switching turns "off" the sensor and turns "on" the stimulator for one or more pulses.

Various triggering algorithms can be developed for effective symptom suppression with animal studies. However, the safety of this invention's procedure has already been established for humans with continuous and higher pulse rates through FDA (Food and Drug Administration) approval. Further, a market also exists for electronic retrofit to thousands of patients who have already been implanted previously, without further brain surgery since the existing DBS electrodes can serve as a two-way bi-directional conductor.

In vitro testing of this approach also can be possible using current systems by sensing electro-magnetic forces from subcutaneous wires of a neurological event onset, such as the beginning of a tremor. These signals, then in turn, can allow the triggering of the existing magnetic switch for turn "off" and "on."

Other types of triggering mechanisms can include those described in U.S. Pat. No. 6,539,263 to Schiff; U.S. Pat. No.

6,366,813 to DiLorenzo; U.S. Pat. No. 6,301,492 to Zonenshayn; U.S. Pat. No. 6,038,480 to Hrdlicka et al.; U.S. Pat. No. 5,833,709 to Rise et al.; U.S. Pat. No. 5,716,377 to Rise et al.; and U.S. Pat. No. 5,707,396 to Benabid, which are all incorporated by reference. Additionally, US Patent Applications 20030181954 to Rezai; 20030085684 to Tsukamoto et al.; and 20020188330 to Frans et al., which are all incorporated by reference, FIGS. 10, 10a and 10b shows a layout of the electronic components that can be used in the apparatus of FIGS. 5a, 5b, 6 along with the triggering algorithm of FIG. 9. Referring to FIGS. 5a, 5b, 6, 10, 10a and 10b, the cap 20 can include miniaturized components that include a battery type power supply 110, which provides power to a stimulation generator controller 120, which is triggered by a triggering switch 250 which receives signals from a sensing circuit 140 all of which are connected to electrodes 40-70 on lead line 30 that is implanted into the skull 310 of the patient 300.

The invention can make use of ultra-miniature batteries 110 such as those, manufactured by Advanced Bionics Corp., which are only about 1/35 the size of a standard AA battery and now serve medical implants by emitting electrical micropulses that stimulate nearby nerves. These tiny batteries, or "Bions," can also be can be programmed from outside the body for strength and frequency of the stimulation, and wirelessly recharged with an electrical field. The use of these ultra-miniature batteries would avoid both a chief source of complaints; the remotely implanted card-deck sized stimulator/battery [about 60 by about 80 by about 15 mm] in the chest area, its replacement, while also avoiding problems associated with vulnerable wire leads under the skin from the chest area to connect with the implant on the skull.

The Stimulation Generator Controller 120 can be a solid-state device such as the one shown and described in the Medtronic's Model 3628 cited 0093 of U.S. Published Patent Application No. 2002/0183817 to Van Venrooij et al., which is incorporated by reference. Trigger Switch 130 can be a common mini-double throw "on-off" and "off-on" electronic switch, triggering based on sensing circuit threshold. The Sensing Circuit 140 can be a common solid-state impulse counter-clock, e.g. mini-version of cardiac-alarm, monitoring electrical impulses to heart The circuits are powered by miniature battery 110 as shown in FIG. 10b. The sensing circuit 140 can include the noise amplitude filter 220 and impulse counter 230 of FIG. 9. The trigger switch 130 is activated when threshold circuit 240 of FIG. 9 is exceeded to turn "off" the sensor input and turn "on" the stimulation generator 120. This is reversed when the impulse is blocked, dropping below threshold.

The components to run the novel invention can be fit into a space of approximately 60 mil by 15 mil compared to prior art. Conservatively less than 50% of the current 60 by about 80 by about 15 mm in a plastic skull-cap implant see FIG. 6.

The invention can be less expensive than the current techniques, since no surgery tunneling down the neck into the chest area is needed for the battery cards, and thus no repairs or surgery for those components—which currently about $10,000 every 3-5 years.

Benefits of using the novel triggering algorithm of FIG. 9 and apparatus components of FIGS. 5a, 5b, 6, 10 and FIGS. 11a-11c,12a-12c.

Figure 11A:
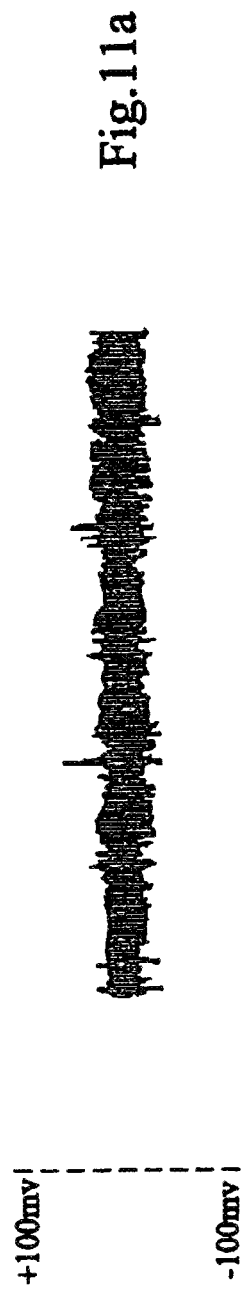
FIG. 11a shows a trace graph of the neuronal impulse bursts in milli-volts verses time of a patient being treated with a Medtronic type (prior art) technique.
Figure 11B:
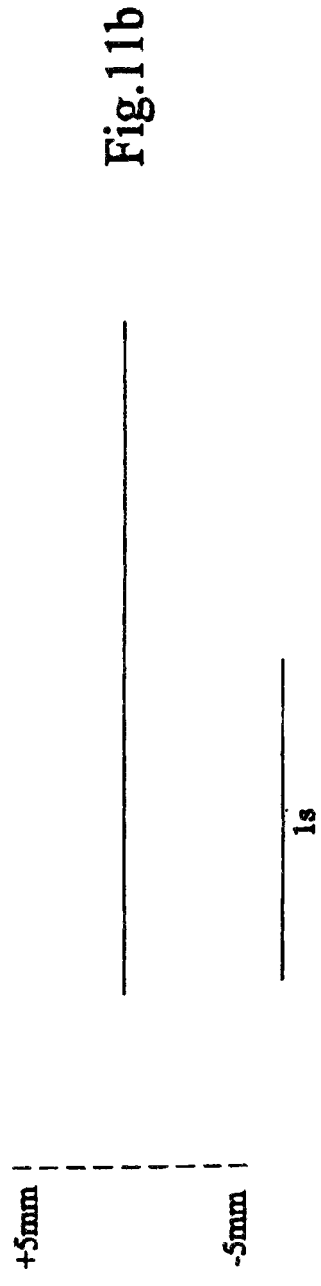
FIG. 11b shows a trace graph of the associated tremor displacement for FIG. 11b verses time of the patient being treated with the Medtronic type (prior art) technique.
Figure 11C:
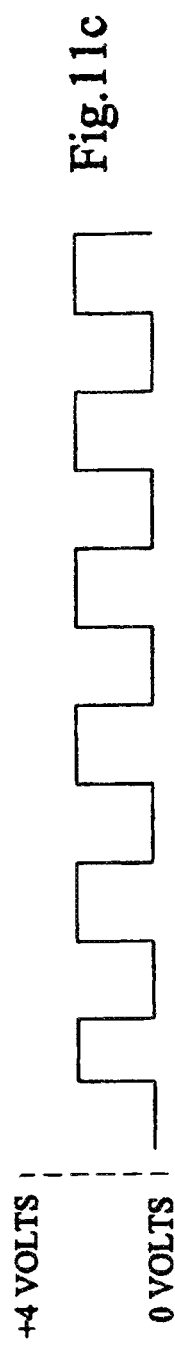
FIG. 11c shows the continuing pulse train that occurs with the Medtronic type (prior art) technique which causes the trace graphs of FIGS. 11a-11b.

FIG. 11a shows a trace graph of the neuronal impulse bursts in mill volts verses time of a patient being treated with a Medtronic type (prior art) technique such as the one shown and described in reference to U.S. Patent Application Publication 2002/0183817 to Van Venrooij et al., which is incorporated by reference. FIG. 11b shows a trace graph of the associated tremor displacement for FIG. 11b verses time of the patient being treated with the Medtronic type (prior art) technique. FIG. 11c shows the continuing pulse train that occurs with the Medtronic type (prior art) technique which causes the trace graphs of FIGS. 11a-11b.

Referring to FIGS. 11a-11c, results in a continuing pulse train (FIG. 11c) in order to cause the effects of no impulse bursts (FIG. 11a) and no resultant physical tremors (FIG. 11b). As described in the background section of this invention this technique requires continuously generating pulsed type signals once the electrodes are activated whether or not a brain type tremor has ended, which would result in needless and excessive, unwanted and potentially dangerous electrical current being continuously generated inside the brain. The more unnecessary pulse type signals, the more undesirable side effects to the patient.

Additionally, the technique proposed in this patent application publication would require excessive power to operate, which are not only expensive since battery power supplies would need to be constantly replaced but also require large card size batteries that must be externally mounted outside of a patient or mounted inside of the upper chest or be constantly connected to an external power supply. This proposed Medtronic technique would also be prone to short circuit since the electrodes would be simultaneously operating as both transmitters and sensors, which also causes excessive and unnecessary power drain, which also shortens the lifespan of any batteries being used as well as increase the costs for replacing the batteries.

FIG. 12a shows a trace graph of the neuronal impulse bursts in mill volts verses time of a patient being treated from being treated by the subject invention described above. FIG. 12b shows a trace graph of the associated tremor displacement for FIG. 12a verses time of the patient being treated by the subject invention. FIG. 12c shows the single pulses that occur with the subject invention technique which results in the trace graphs of FIGS. 12a-12b.

Referring to FIGS. 12a-12c, the invention causes single spaced apart pulses to occur over greater periods of time, where each pulse occurs on-demand, and not as a continuous series of pulses. As shown by FIG. 12a, the initial impulse burst and subsequent impulse bursts have long delay time periods there between, which can result in substantially reduced or eliminated tremors resulting therefrom, FIG. 11b.

The novel invention allows for less undesirable electrical current to be generated within the brain, less side effects that result therefrom, less power consumption as well as other apparent benefits. The novel invention can use small batteries that were not able to be used in the prior art systems and techniques, and also results in power supplies that require less replacements as well. The novel invention is able to eliminate the need for large and cumbersome card type batteries or external power supplies, and results in a better system for treatment.

Differences between the subject invention and that described in the Medtronic technique shown in U.S. Patent Application Publication 2002/0183817 to Van Venrooij et al. are compiled in Table 1.

TABLE 1

Comparison of prior art (Medtronic) and Invention.

| ATTRIBUTE | MEDTRONIC | INVENTION |
| --- | --- | --- |
| Sensing | Loss of Effectiveness | Single Event |
| Trigger | Brain "Activity" | Initial Impulse Burst |

TABLE 1-continued

Comparison of prior art (Medtronic) and Invention.

| ATTRIBUTE | MEDTRONIC | INVENTION |
| --- | --- | --- |
| Objective | Select Electrodes | Stop Single Tremor |
| Stimulator | Normally-On | Normally-Off |
| Power | No "off" (continuing pulses) Large Battery | Only "on" as needed (individual pulse) Small Battery |
| Power Lifespan | Limited | Extended |
| Battery Mounting | Implantable" | Skull - Mounted in Cap |
| Side Effects | Continuous electrical current | Limited Electrical Current |

Besides circuitry miniaturization, by triggering pulse generation only when needed, fewer pulses per second also can reduce some of the mild, but known side effects of DBS, and the timed delivery also can delay the onset of the next event by physiological feedback, that is also known to be effective against a known clinical phenomena Parkinson's Disease.

Other advantages can also be realized. The timed pulse feedback speculatively could induce the brain to adaptively alter actual neural circuitry, allowing a further reduction of pulse rate and even more efficiency or even better help reduce symptoms naturally, just as brain circuitry is known to be altered by experience.

While the invention has been described for use with tremors, the invention can have applicability to other medical applications, such as but not limited to movement disorders and cardiac dysfunctions, but extends to include other neurological diseases and disorders such as epilepsy, psychiatric and behavioral dysfunctions such as schizophrenia and drug-induced symptoms and the like.

Figure 13:
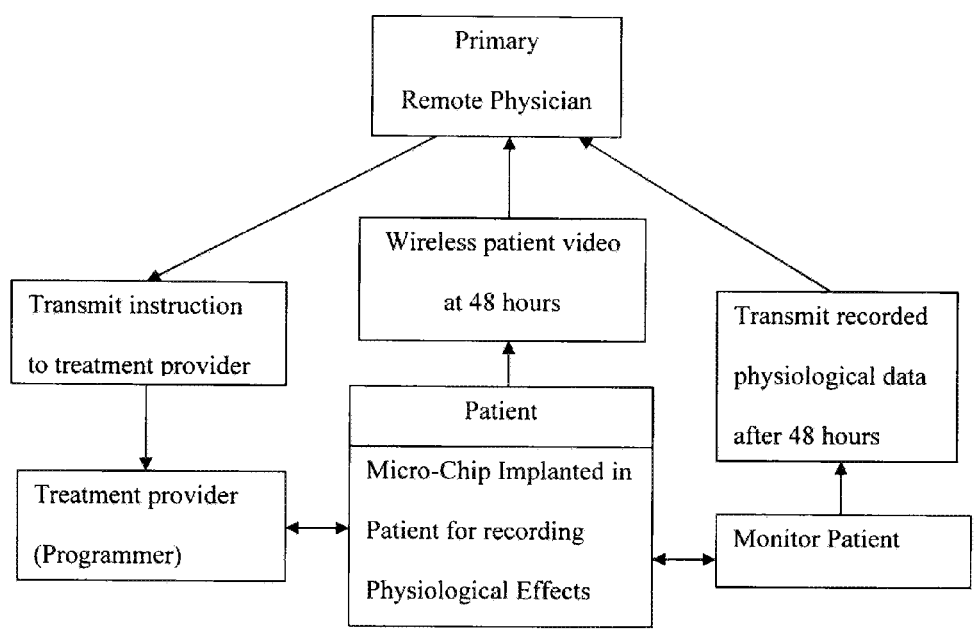
FIG. 13 is a block diagram showing the interface between the implanted deep brain stimulation device, a treatment provider (programmer) and a remote physician.

FIG. 13 is a block diagram showing a preferred embodiment of a deep brain stimulation implant that includes an interface with a treatment provider (programmer) and a remote physician. The deep brain stimulation device implants electrodes in the brain and attaches the electrodes to a battery-operated neurostimulator (or pulse generator), which sends impulses to correct the abnormal brain activity. The deep brain stimulator device of the present invention provides more versatile treatments from the electrodes since the vertically oriented electrodes (transducers) can be switched back and forth from sensing (receiving) to transmitting treatment pulses. As shown in FIG. 13, the implanted deep brain stimulator of this embodiment also includes an interface with a treatment provider (programmer) and a remote physician for monitoring and modifying the treatment.

Currently, treatments may take place weekly, but there is no direct feedback from the patients on the results of the treatments, and physicians do not have adequate data to modify the treatments to make treatment more effective. For example, the current treatments do not use the Unified Parkinson Diagnosis Rating Schedule (UPDR scale) to record the results of the treatments and determine modification to the treatments. Also, current implant treatments with electrodes require at least 48 hours to see the effects of the treatment. Currently, there is no realtime measuring data available for the treating physician to see the results of the treatments.

As described in the previous embodiment, when an event, or tremor, is sensed, the implant can deliver a mild electrical inhibiting pulse(s) to an area of the patient's brain responsible for the event to suppress the event's full expression. In this embodiment, the deep brain stimulation methods, systems and devices interfaces a treatment provider and a remote physician with the patient. Referring to FIGS. 5a-5b and 6, the hole cap 20 includes a top cover 20T, and bottom cylindrical disc housing 20B to house components 100 to monitor the effects of treatment and to modify treatments. Underneath the cap 20 can be a processor based neurostimulator with memory coupled with a lead line 30, and approximately four (4) directional transducers (electrodes) 40, 50, 60 and 70 integral with the deep brain stimulator implant.

After implantation of the deep brain stimulator, there is a requirement for programming or adjusting of the stimulator that can take as much as six hours in selected cases and involve multiple sessions with the patient. According to the present invention, the triggering events and the deep brain stimulator response to the events can be recorded for a period of time, for example, at least 48 hours. At the same time, the patient can be positioned within range of a computer based camera to provide visual data corresponding to the physiological feedback data from the implant. The recorded physiological and visual data can be accessed by a remotely located physician over the world wide web (Internet). For example, an online video call can be placed between the remote physician and the patient using an online telephone service such as but not limited to SKYPE®, by Skype Limited Corporation. During the online video call, the remote physician receives visual feedback of the patient and can notice distinct changes in the patient's facial expressions and ability to walk, talk and perform other everyday activities.

Currently, implant providers use technicians (such as programmers) as the treatment providers to patients. These treatment providers enable the electrodes on the implant to sense tremors and to excite the electrodes to treat the areas of the brain that the tremors come from. At the same time, the remote physician receives visual feedback through the online video call. Using both the physiological and visual feedback, the remote physician can provide directions to the treatment provider to vary the treatment.

Current implant treatments with electrodes need at least approximately 48 hours to see the effects of the treatment. With the deep brain stimulation device of the present invention, the remote physician can monitor the treatment from a remote location by checking both recorded physiological feedback and real time visual feedback of the patient during the 48 hour window after a treatment. Using the direct feedback from the patient, the results of the treatment can be analyzed by the remote physician to make sure the treatment is effective.

Recorded physiological feedback allows the remote physician to monitor the electrical cellular signatures from the brain receiving the treatments, and monitor the effects over the 48 hour window with a device, such as but not limited to an oscilloscope. In this embodiment of the invention, the implant is modified to include an integrated circuit in the cap of the implant that records the electrical cellular signatures from the brain during at least a 48 hour window. At the end of the 48 hour window, all the signatures that occurred during this window can be automatically transmitted via the world wide web from the deep brain stimulation implant to the remote physician. The totals of the electrical cellular signature, can be averaged over the 48 hour window for use in determining the effectiveness of the treatment.

Using visual feedback at the end of the 48 hour window, the remote physician can visually see the patient, using a realtime visual communication medium such as SKYPE®, and the like, where a camera provides a realtime video feed of the patient to allow the remote physician to see the effects of the treatment 48 hours after the treatment.

The visual feedback will show facial feature changes and speech changes that have occurred 48 hours after the treatment. Adding visual feedback to the physiological data available to the remote physician, allows the physician to use the Unified Parkinson Diagnosis Rating Scale (UPDR scale) to rate the patients mentation, daily living and motor skills for use in determining treatment. Providing access to physiological and visual feedback data on demand allows the remote physician to tailor treatment in response to current patient needs to make the treatments more effective.

Based on the electrical cellular signatures from the physiological feedback (electro physiological signals) from the deep brain stimulation implant, which are averaged over a 48 hour window and sent to the remote physician, and the visual feedback of the patient being shown to the RP 48 hours after the treatment, the RP can then adjust the electrodes as needed for the next treatment period. A simple neurostimulator is one capable of affecting three or fewer of the following: pulse amplitude, pulse duration, pulse frequency, electrode contacts, cycling, stimulation train duration, train spacing, number of programs, number of channels, phase angle, alternating electrode polarities, configuration of wave form, or more than one clinical feature. A complex neurostimulator is one capable of affecting more than three of the above.

Using the recorded data, a remote physician can control, or "tweak", one or more of the electrodes on the deep brain stimulation implant. The remote physician, for example, can vary the amplitude, pulse width and/or frequency of the stimulation pulse(s) in response to a particular event(s). When necessary the remote physician can switch electrodes between anodes and cathodes, based on the monitoring.

There are many benefits of the remote physician monitoring the effect the treatment has on the patient including unified and standardized treatments of patients, where different patients at different locations can receive uniform and more standardized treatments to optimize results; control of the patient treatments by a physician and not by a treating technician (programmer); and reducing patients pain from Dystonia which is a neurological movement disorder, in which sustained muscle contractions cause twisting and repetitive movements or abnormal postures.

The deep brain stimulator device of the present invention provides more versatile treatments from the electrodes since the vertically oriented electrodes can be switched back and forth from sensing (receiving) to transmitting treatment pulses, where the prior art generally required separate sensing electrodes and separate transmitting electrodes. Problem with prior art, is the brain area to be treated did not receive a treatment pulse from the same electrode which sensed the tremor. According to the present invention, one electrode from the plurality that sensed the tremor, can be the same electrode that is switched to a transmit function to transmit a treatment pulse(s) targeted for the area generating the tremor.

With a single vertical arrangement of at least four electrodes, the deep brain stimulation device software can be programmed such that the one electrode that senses the tremor can be the same electrode that transmits an electrical pulse in response to the tremor. However, the stimulation device can be programmed to provide different treatments as needed to effect maximum and successful treatment using the four vertical oriented electrodes. For example, the same sensing electrode can be switched to transmit and send the treatment pulses. Alternatively, sensing electrode and another one of the electrode cab be switched to transmit to both send a treatment pulses, or the sensing electrode and two or three other electrodes can be switched to transmit and all send treatment pulses. This versatility gives the remote physician greater power to effect treatment in the targeted area.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A system for providing deep brain stimulation in response to a sensed brain tremor, comprising:
   a single cylindrical disc housing with a single bottom housing with side edges and a single removable top with perimeter side edges that overlap the side edges of the single bottom housing,
   a single elongated lead extending between a center portion of the bottom of the single cylindrical disc housing with a plurality of electrodes with each electrode being used to both sense a single brain tremor and generate pulses therefrom, wherein at least one of the electrodes senses the tremor, and at least the same electrode generates the pulses therefrom targeting a location which emits the single brain tremor, the single lead being adapted to be implanted into only a single opening in the skull while the single cylindrical disc housing remains mounted as cap on top of the skull of the user,
   a pulse stimulator inside a compartment of the single cylindrical disc housing and only being activated to generate a pulse stimulation upon sensing a tremor from one of the plurality of electrodes,
   a sensing detection circuitry,
   controls for activating the pulse stimulator upon sensing of the single brain tremor and deactivating the pulse stimulator when a tremor is not being sensed,
   a battery power supply for providing power to the pulse stimulator only upon sensing the single brain tremor and along with the controls turning off the pulse stimulator after the sensing detection circuitry has been turned on;
   a processing device with memory to execute a set of instructions to record physiological data of the sensed tremor and a response to the sensed tremor; and
   an interface for downloading the recorded physiological data.

2. The system of 1, wherein the plurality of electrodes includes:
   four electrodes for transmitting and receiving on the single elongated lead.

3. The system of claim 1, wherein, at least two of the electrodes senses the tremor, and at least one of the two electrodes generates the pulses therefrom targeting a location which emits the single brain tremor.

4. The system of claim 1, wherein the interface is a wireless interface to automatically transmit recorded physiological data to an external computer.

5. The system of claim 1, wherein the interface is a wireless interface to allow a treatment provider to modify the response to the sensed tremor.

6. A system for providing deep brain stimulation in response to a sensed brain tremor, comprising:
   a single cylindrical disc housing with a single bottom housing with side edges and a single removable top with perimeter side edges that overlap the side edges of the single bottom housing,
   a single elongated lead extending between a center portion of the bottom of the single cylindrical disc housing with a plurality of electrodes with each electrode being used to both sense a single brain tremor and generate pulses therefrom, wherein at least one of the electrodes senses the tremor, and at least the same electrode generates the pulses therefrom targeting a location which emits the single brain tremor, the single lead being adapted to be implanted into only a single opening in the skull while the single cylindrical disc housing remains mounted as cap on top of the skull of the user, a pulse stimulator inside a compartment of the single cylindrical disc housing and only being activated to generate a pulse stimulation upon sensing a tremor from one of the plurality of electrodes, a sensing detection circuitry, controls for activating the pulse stimulator upon sensing of the single brain tremor and deactivating the pulse stimulator when a tremor is not being sensed, a battery power supply for providing power to the pulse stimulator only upon sensing the single brain tremor and along with the controls turning off the pulse stimulator after the sensing detection circuitry has been turned on; and a video camera to provide visual feedback of a patient receiving deep brain stimulation via an internet connection to a remote location physician.

7. The system of claim 6, wherein the internet connection is an online video telephone service transmitting realtime audio and video.

8. A deep brain stimulation system with remote monitoring controls, comprising:

a cap mounted housing having an elongated lead extending from the cap mounted device, the lead adapted to be implanted into a head of a patient, a plurality of electrodes on the lead for sensing tremors and generating pulses therefrom directed toward the tremors, wherein at least one of the electrodes senses at least one of the tremors, and at least the same electrode generates the pulses therefrom targeting a location which emits the brain tremors sensed;

a processor based controller having monitoring instructions for sensing initiation of an unwanted electro-physiologically signaled event and recording the event in memory, and a set of triggering instructions for activating a stimulator to generate at least one treatment pulse from the electrodes and record physiological data from the treatment pulse in the memory, a transmission medium for sending the recorded physiological data to a remote monitoring location, and another transmission medium for sending treatment instructions to a treatment provider station for modifying the monitoring and triggering sets of instructions in the processor.

9. The system of claim 8, further comprising:

a video camera for providing feedback images via an internet connection to the remote monitoring location, wherein the treatment instructions are based on both the recorded physiological data and the visual feedback images.

* * * * *